US008278483B2

(12) United States Patent
Mahidhar et al.

(10) Patent No.: US 8,278,483 B2
(45) Date of Patent: Oct. 2, 2012

(54) PROCESS FOR SYNTHESIS OF GLYCOMIMICKING CATIONIC AMPHIPHILES

(75) Inventors: Yenugonda Venkata Mahidhar, Hyderabad (IN); Arabinda Chaudhuri, Ghaziabad (IN); Rama Mukherjee, Ghaziabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 624 days.

(21) Appl. No.: 12/160,203

(22) PCT Filed: Feb. 7, 2007

(86) PCT No.: PCT/IB2007/000281
§ 371 (c)(1), (2), (4) Date: Apr. 20, 2009

(87) PCT Pub. No.: WO2008/001166
PCT Pub. Date: Jan. 3, 2008

(65) Prior Publication Data
US 2009/0306213 A1    Dec. 10, 2009

(30) Foreign Application Priority Data
Feb. 7, 2006   (IN) ............................ 359/DEL/2006

(51) Int. Cl.
*C07C 231/02*   (2006.01)
*C07C 233/05*   (2006.01)
(52) U.S. Cl. ...................... 564/138; 564/183; 564/189
(58) Field of Classification Search ................. 564/138, 564/183, 189
See application file for complete search history.

(56) References Cited

U.S. PATENT DOCUMENTS

| 4,897,355 A | 1/1990 | Eppstein et al. ........... 435/240.2 |
| 4,946,787 A | 8/1990 | Eppstein et al. ........... 435/240.2 |
| 5,264,618 A | 11/1993 | Felgner et al. ................ 560/224 |
| 5,283,185 A | 2/1994 | Epand et al. ................ 435/172.3 |
| 5,527,928 A | 6/1996 | Nantz et al. .................... 554/105 |
| 5,614,503 A | 3/1997 | Chaudhary et al. ............. 514/44 |
| 5,661,018 A | 8/1997 | Ashley et al. .............. 435/172.3 |
| 5,686,620 A | 11/1997 | Ashley et al. ................. 548/113 |
| 5,688,958 A | 11/1997 | Ashley et al. ................. 548/113 |
| 5,698,721 A | 12/1997 | Heath ............................. 554/80 |
| 5,705,693 A | 1/1998 | DePrince et al. ............. 564/159 |
| 5,719,131 A | 2/1998 | Harris et al. .................... 514/44 |
| 6,333,433 B1 | 12/2001 | Banerjee et al. .............. 564/296 |
| 6,346,516 B1 | 2/2002 | Banerjee et al. ................ 514/44 |
| 6,503,945 B2 | 1/2003 | Banerjee et al. ............... 514/547 |
| 6,509,032 B1 | 1/2003 | Huang et al. .................. 424/450 |
| 6,541,649 B2 | 4/2003 | Banerjee et al. .............. 554/114 |
| 6,583,131 B2 | 6/2003 | Deshmukh et al. ........... 514/176 |
| 6,586,410 B1 | 7/2003 | Wheeler et al. ................. 514/44 |
| 6,627,218 B2 | 9/2003 | Huang et al. .................. 424/450 |

OTHER PUBLICATIONS

"Animal Cell Culture: a Practical Approach", Second Edition, Oxford/New York, IRL Press, Oxford University Press, 5-20, 1977.
Felgner et al., "Enhanced gene delivery and mechanism studies with a novel series of cationic lipid formulations," *J. Biol. Chem.*, 269 (4): 2550-2561, 1994.
Felgner et al., "Lipofection: a highly efficient, lipid-mediated DNA-transfection procedure," *Proc. Natl. Acad. Sci. U.S.A.*, 84 (21): 7413-7417, 1987.
International Search Report, issued in Int. App. No. PCT/IB2007/000281, mail date Nov. 2, 2008.
Karmali et al., "Design Syntheses and in Vitro Gene Delivery Efficacies of Novel Mono-, Di- and Trilysinated Cationic Lipids: A Structure-Activity Investigation," *J. Medicinal Chem.*, 47 (8): 2124, 2004.
Kumar et al., "Single histidine residue in head-group region is sufficient to impart remarkable gene transfection properties to cationic lipids: evidence for histidine-mediated membrane fusion at acidic pH," *Gene. Ther.*, 10 (15): 1206-1215, 2003.
Leventis and Silvius, "Interactions of mammalian cells with lipid dispersions containing novel metabolizable cationic amphiphiles," *Biochem. Biophys. Acta.* 1023 (1): 124-132, 1990.
Schoen et al., "Gene transfer mediated by fusion protein hemagglutinin reconstituted in cationic lipid vesicles," *Gene Ther.*, 6 (5):823-832, 1999.
Solodin et al., "A novel series of amphiphilic imidazolinium compounds for in vitro and in vivo gene delivery," *Biochemistry*, 17 (34): 16537-16544, 1995.
Wheeler et al., "A novel cationic lipid greatly enhances plasmid DNA delivery and expression in mouse lung,", *Proc. Natl. Acad Sci. U.S.A.*, 93 (21), 11454-11459, 1996.

*Primary Examiner* — Shailendra Kumar
(74) *Attorney, Agent, or Firm* — Fulbright & Jaworski L.L.P.

(57) ABSTRACT

The present invention provides processes for the synthesis of novel Shikimic acid head-group containing non-toxic cationic amphiphiles capable of facilitating transport of biological macromolecules into cells.

12 Claims, 8 Drawing Sheets

Lipid1:Chol (1:1)

FIG. 6A

Lipid1

FIG. 6B

Lipid2:Chol (1:1)

FIG. 6C

Lipid2

FIG. 6D

PROCESS FOR SYNTHESIS OF GLYCOMIMICKING CATIONIC AMPHIPHILES

This application is a national phase application under 35 U.S.C. §371 of International Application No. PCT/IB2007/000281 filed 7 Feb. 2007, which claims priority to Indian Patent Application No. 359/DEL/2006 filed 7 Feb. 2006. The entire text of each of the above-referenced disclosures is specifically incorporated herein by reference without disclaimer.

FIELD OF THE INVENTION

The present invention relates to processes for preparing novel cationic amphiphiles containing Shikimic acid head group. The invention provides novel compositions containing the said amphiphiles that are useful to facilitate transport of biologically active molecules into cells. The area of medical science that is likely to benefit most from the present invention is gene therapy.

BACKGROUND OF THE INVENTION

The present invention relates to process for the synthesis of novel cationic amphiphilic compounds that facilitate the intracellular delivery of therapeutic biological macromolecules. The present invention also relates to new compositions comprising such cationic amphiphiles those are useful for delivering biological macromolecules into body cells. The novel cationic lipids of the present invention are particularly useful to combat genetic diseases by non-viral gene therapy.

Many defective genes associated with numerous genetic diseases have been identified and characterized. However, since the biological cell membranes are semi-permeable in nature, delivering the required amounts of therapeutically important correct genes into the target body cells is often a daunting challenge. Thus, success of gene therapy approach in treating genetic diseases depends, in a major way, on the development of efficient and safe gene delivery reagents that will facilitate the intracellular delivery of therapeutic genes into the particular body cells of a patient. Accordingly, development of safe and efficient gene delivery reagents and methods that can facilitate entry of functional genes into body cells are of great medical importance.

PRIOR ART

Amphiphatic molecules having both polar and non-polar regions in their molecular architectures are efficacious in delivering therapeutically important biological macromolecules into cells. This makes sense given the existence of both polar and non-polar segments in biological cell membranes. Cationic amphiphiles are the particularly important class of amphiphilic compounds used most extensively for enhancing intracellular delivery of many biologically active therapeutic compounds. At physiological pH, the polar segment of cationic amphiphiles interacts with the therapeutically important molecules including polyanionic macromolecular DNA, RNA, proteins etc. while the non-polar region of the cationic amphiphiles facilitates the passage of the therapeutic biomolecules through the non-polar part of the cell membranes.

The following references are examples of processes for the synthesis of cationic amphiphiles that are known in the art to be useful for enhancing the intracellular delivery of therapeutically important biological macromolecules. In addition to the molecular structures, these prior arts contain useful information and discussion on the properties of the cationic amphiphiles those are believed to be responsible for their carrier properties.

Felgner et al., *Proc. Natl. Acad. Sci. U.S.A.*, 84, 7413-7417 (1987), reported the first use of a highly efficient cationic lipid N-[1-(2,3-dioleyloxy)propyl]-N,N,N-trimethyl ammonium chloride(DOTMA) as the DNA transfection vector.

U.S. Pat. Nos. 4,897,355 and 4,946,787 (1990) reported the synthesis and use of N-[.omega.(.omega.-1)-dialkyloxy]- and N-[.omega.(.omega.-1)-dialkenyloxy]-alk-1-yl-N,N,N-tetrasubstituted ammonium amphiphiles and their pharmaceutical formulation as efficient transfection vectors.

Leventis, R. and Silvius, J. R. *Biochim. Biophys. Acta.* 1023, 124-132, (1990) reported the interactions of mammalian cells with lipid dispersions containing novel metabolizable cationic amphiphiles.

U.S. Pat. No. 5,264,618 (1993) reported the synthesis and use of additional series of highly efficient cationic lipids for intracellular delivery of biologically active molecules.

Felgner et al. *J. Biol. Chem.* 269, 2550-2561 (1994) reported enhanced gene delivery and mechanistic studies with a novel series of cationic lipid formulations.

U.S. Pat. No. 5,283,185 (1994) reported the synthesis and use of 3β[N—(N',N'-dimethylaminoethane)carbamoyl]cholesterol, termed as "DC-Chol" for delivery of a plasmid carrying a gene for chloramphenicol acetyl transferase into cultured mammalian cells.

U.S. Pat. No. 5,283,185 (1994) reports use of N-[2-[[2,5-bis[(3-aminopropyl)amino]-1-Oxopentyl]aminoethyl]-N,N-dimethyl-2,3-bis-(9-octadecenyloxy)-1-Propanaminium tetra (trifluoroacetate), one of the most widely used cationic lipids in gene delivery. The pharmaceutical formulation containing this cationic lipid is sold commercially under the trade name "Lipofectamine".

Solodin et al. *Biochemistry* 34,13537-13544, (1995) reported a novel series of amphilic imidazolinium compounds for in vitro and in vivo gene delivery.

Wheeler et al. *Proc. Natl. Acad. Sci. U.S.A.* 93, 11454-11459, (1996) reported a novel cationic lipid that greatly enhances plasmid DNA delivery and expression in mouse lung.

U.S. Pat. No. 5,527,928, (1996) reported on the synthesis and transfection biology of a novel cationic lipid namely, N,N,N',N'-tetramethyl-N,N'-bis(2-hydroxyethyl)-2,3-di(oleoyloxy)-1,4-butaneammonium iodide. U.S. Pat. No. 5,527, 928 (1996) reported the synthesis and the use of N,N,N,N-tetramethyl-N,N-bis(hydroxy ethyl)-2,3-di(oleolyoxy)-1,4-butanediammonim iodide i.e. pharmaceutical formulation as transfection vector. U.S. Pat. No. 5,698,721 (1997) reported the synthesis and use of alkyl O-phosphate esters of diacylphosphate compounds such as phosphatidylcholine or posphatidylethanolamine for intracellular delivery of macromolecules. U.S. Pat. Nos. 5,661,018; 5,686,620 and 5,688, 958 (1997) disclosed a novel class of cationic phospholipids containing phosphotriester derivatives of phosphoglycerides and sphingolipids efficient in the lipofection of nucleic acids. U.S. Pat. No. 5,614,503 (1997) reported the synthesis and use of an amphiphatic transporter for delivery of nucleic acid into cells, comprising an essentially nontoxic, biodegradable cationic compound having a cationic polyamine head group capable of binding a nucleic acid and a cholesterol lipid tail capable of associating with a cellular membrane. U.S. Pat. No. 5,705,693 (1998) disclosed the method of preparation and use of new cationic lipids and intermediates in their synthesis that are useful for transfecting nucleic acids or peptides into prokaryotic or eukaryotic cells. These lipids comprise one or two substituted arginine, lysine or ornithine residues, or derivatives thereof, linked to a lipophilic moiety. U.S. Pat. No. 5,719,131 (1998) has reported the synthesis of a series of novel cationic amphiphiles that facilitate transport of genes into cells. The amphiphiles contain lipophilic groups derived from steroids, from mono or dialkylamines, alkylamines or polyalkylamines. U.S. Pat. No. 6,333,433 (2001) has reported a process for the synthesis of novel cationic amphiphiles containing N-hydroxyalkyl group for intracellular delivery of biologically active molecules. U.S. Pat. No. 6,346,516 (2002) has reported on development of novel cationic amphiphiles containing N-hydroxyalkyl group for intracellular delivery of biologically active molecules. U.S. Pat. No. 6,627,218 (2003) has reported development of a stable aqueous dispersion of a cholesterol-derived cationic lipid containing a biodegradable base-resistant linker functionality, a spacer arm and an cationic amine head-group capable of transferring nucleic acids into biological cells. U.S. Pat. No. 6,586,410 (2003) disclosed novel lipid-nucleic acid particulate complexes which are useful for in vitro or in vivo gene transfer. U.S. Pat. No. 6,583,131 (2003) disclosed cationic cholesteryl derivatives bearing a nitrogen-containing ring structure as their polar head group. These compounds are useful for delivering biologically active substances to cells and for transfecting nucleic acids into cells. U.S. Pat. No. 6,541,649 (2003) reports a process for synthesis of novel cationic amphiphiles containing N-hydroxyalkyl group for intracellular delivery of biologically active molecules. U.S. Pat. No. 6,509,032 (2003) discloses a cationic lipid useful in transfection of cells with DNA. U.S. Pat. No. 6,503,945 (2003) reports a process for synthesis of novel cationic amphiphiles containing N-hydroxyalkyl group for intracellular delivery of biologically active molecules.

SUMMARY OF THE INVENTION

The present invention provides a process for the synthesis of cationic lipids having the structure A

A wherein each of $R_1$ and $R_2$ is independently hydrogen or a lipophilic moiety containing at least eight carbon atoms and is optionally selected from 8-22 carbon containing alkyl, mono-, di- and tri-unsaturated alkenyl ($C_8$-$C_{22}$) provided both $R_1$ and $R_2$ are not hydrogen; $R_3$ is an alkyl group ($C_1$-$C_5$, straight or branched); n is an integer between 7 and 21 and X is optionally selected from chlorine or bromine atom.

In one embodiment of the invention, n=13 or 15, $R_3$ are independently selected from methyl, ethyl or n-propyl groups and $X^-$ is selected from chloride or bromide ions.

In another embodiment of the invention, the amphiphile is of the formula 1 or 2 given below:

1

2

In another embodiment of the invention, lipophilic $R_1$ and $R_2$ groups are selected from the group consisting of saturated $C_8$-$C_{22}$ alkyl groups and unsaturated $C_8$-$C_{22}$ alkenyl groups containing 1, 2, or 3 double bonds.

The present invention also relates to a process for the synthesis of Shikimic acid head-group based cationic amphiphiles of the structural formula A:

A wherein each of $R_1$ and $R_2$ is independently hydrogen or a lipophilic moiety containing at least eight carbon atoms and is optionally selected from 8-22 carbon containing alkyl, mono-, di- and tri-unsaturated alkenyl ($C_8$-$C_{22}$) provided both $R_1$ and $R_2$ are not hydrogen; $R_3$ is an alkyl group ($C_1$-$C_5$, straight or branched); n is an integer between 7 and 21 and X is optionally selected from chlorine or bromine atom, said process comprising the steps of:
(a) coupling a mixed primary-tertiary lipophilic aliphatic alkyl amine containing saturated or unsaturated aliphatic hydrocarbon chains with Shikimic acid in polar aprotic solvents in presence of amide bond forming reagents to obtain the corresponding aliphatic hydrophobic amide intermediate;
(b) quaternizing the hydrophobic amide obtained in step (a) with excess of appropriate alkyl iodides to obtain corresponding quaternized amphiphilic ammonium iodides intermediate;
(c) subjecting the quaternized amphiphilic intermediate obtained in step b to ion exchange chromatography halide ion exchange resins and mixed polar organic solvent as eluent.

In one embodiment of the process, saturated or unsaturated aliphatic hydrocarbon chains of mixed primary-tertiary amine is selected from group consisting of 8-22 C atoms.

In another embodiment of the invention, the polar aprotic solvents in which the reaction is carried out in step (a) of claim 1 is selected from the group comprising dimethyl formamide, dimethylsulphoxide, pyridine, triethyl amine.

In another embodiment of the invention, the reaction of step (a) is carried out at a temperature between 0° C. to 80° C.

In another embodiment of the invention, the quaternization of the intermediate hydrophobic amide obtained in step (a) is carried out at temperature between −10° C. to 50° C.

In another embodiment of the invention, the halide ion exchange resins used in step (c) is selected from the chloride or bromide ion exchange resins.

In another embodiment of the invention, the organic solvents used as ingredients of the polar eluent in step (c) is selected from the group consisting of methanol, ethanol, chloroform, dichloro methane and ethyl acetate.

The present invention also relates to a method for gene therapy using facilitated transport of biologically active molecules into cells comprising administering to a patient in need of gene therapy a shikimic acid head group based cationic amphiphile of the formula A above contained in a pharmaceutically acceptable carrier.

DETAILED DESCRIPTION OF THE INVENTION

The present invention relates to process for the synthesis of novel shikimic acid head-group containing cationic amphiphiles. The novel cationic amphiphiles containing polar glyco-mimicking shikimic acid head groups are potentially useful to deliver into the cells of patient therapeutically effective amounts of biologically active molecules. The area of science that will benefit most from the present invention is non-viral gene therapy.

The distinctive novel structural features common to the cationic amphiphiles disclosed in the present invention include: (1) The presence of hydrophobic groups which are directly linked to the positively charged nitrogen atom; (2) the presence of glyco-mimicking polar shikimic acid head-group; (3) unlike many other commercially available glycerol-backbone based cationic amphiphiles used in delivering genes into cells, the presently disclosed cationic lipids do not have any glycerol-backbone in their molecular architectures. It is believed that these unique structural features contribute significantly to the increased gene delivery efficiencies of the cationic amphiphiles disclosed herein.

According to the practice of the present invention, "cationic" means the positive charge is either on quaternized nitrogen or on a protonated nitrogen atom. The cationic characters of amphiphiles contribute to enhanced interaction of amphiphiles with biologically active molecules such as nucleic acids and/or with cell constituents such as plasma membrane glycoproteins. Such enhanced interaction between the cationic amphiphiles and therapeutically active biological macromolecules and/or cell membrane constituents may play a key role in successfully transporting the therapeutic molecules into the cells.

The cationic amphiphiles of the present invention have certain common structural and functional groups. As such, the said cationic amphiphiles may be represented by the following generic formula (A):

wherein each of $R_1$ and $R_2$ is independently hydrogen or a lipophilic moiety containing at least eight carbon atoms and is optionally selected from 8-22 carbon containing alkyl, mono-, di- and tri-unsaturated alkenyl ($C_8$-$C_{22}$) provided both $R_1$ and $R_2$ are not hydrogen; $R_3$ is an alkyl group ($C_1$-$C_5$, straight or branched); n is an integer between 7 and 21 and X is optionally selected from chlorine or bromine atom.

The cationic lipids have a lipophilic domain that facilitates the formation of lipid complexes or aggregates in aqueous solutions. The lipophilicity of the hydrophobic domains and the hydrophilicity of the polar head group domains are such that when the cationic lipids are confronted with aqueous solutions, lipid aggregates are formed in the presence or absence of a second compound. Exemplary lipophilic $R_1$ and $R_2$ groups include (1) saturated $C_8$-$C_{22}$ alkyl groups and (2) unsaturated $C_8$-$C_{22}$ alkenyl groups containing 1, 2, or 3 double bonds.

In one preferred embodiment of the presently disclosed cationic lipids where n=13 or 15, $R_3$ are independently selected from methyl, ethyl or n-propyl groups and $X^−$ is selected from chloride or bromide ions. According to this aspect of the present invention, the following amphiphile Nos. 1 and 2 are two particular examples:

Syntheses of the Cationic Lipids

Scheme I outlines the synthetic strategy employed for preparing the cationic lipid 1 containing two myristyl hydrophobic tails, a Shikimic acid head group and the chloride counterion. The same synthetic scheme is employed to synthesize cationic lipid 2.

Reagents and conditions: (a) EDCI/HOBT/DCM/DMF (b) CH$_3$I/ Chloride ion exchange with A-26

Cationic Lipids 1 and 2 were synthesized by EDCI coupling of the appropriate mixed tertiary-primary amine intermediate (II, Scheme 1, prepared conventionally by reacting the corresponding N,N-di-n-alkyl amine with N-tert-butyloxy carbonyl protected 2-bromoethyl amine in ethylacetate in presence of anhydrous potassium carbonate and followed by deprotection and neutralization) with shikimic acid. The resulting tertiary amine intermediate III (Scheme 1) upon quaternization with excess methyl iodide followed by chloride ion exchange over Amberlyst-26 afforded lipids 1 and 2.

Formulations

The invention also provides novel therapeutic formulation comprising therapeutically effective amounts of the cationic amphiphilic compounds disclosed herein, biological macromolecules and the co-lipids. One or more additional physiologically acceptable substances may be included in the pharmaceutical formulation of the invention to stabilize the formulation for storage or to facilitate successful intracellular delivery of the biologically active molecules. Co-lipids according to the practice of the present invention are useful in mixing with one or more cationic amphiphiles. Cholesterol is an excellent co-lipid for use in combination with the presently described cationic lipids to facilitate successful intracellular delivery of the biologically active molecules. A preferred range of molar ratio of cationic amphiphile to co-lipid is 1:1. As such, it is within the art to vary the said range to a considerably wide extent. Typically, liposomes were prepared by rapidly injecting 70 μL of an ethanol solution of the lipid mixture—chol/lipid 1, chol/lipid 2 (at 1:1 mole ratio) at 1 mM into 930 μL of deionized water. The resulting small unilamellar vesicles (SUV) were stored at room temperature.

Biologically active molecules that can be administered intracellularly in therapeutic amounts using the cationic amphiphilic compound of the present invention include ribosomal RNA, antisense polynucleotide of RNA or DNA, polynucleotide of genomic DNA, cDNA or mRNA that encodes for a therapeutically important protein. The cationic lipids of the present invention may be blended such that one or more of the representatives thereof may be used in a combination to facilitate entry of the said biologically active molecules into cells/tissues.

In a further embodiment, the amphiphiles may be used either in pure form or in combination with other lipids or helper lipids such as cholesterol, phosphatidylethanolamine, phosphatidylglycerol, etc. The said therapeutic formulation may be stored at 0° C.-4° C. until complexed with the biologically active therapeutic molecules. Agents that prevent bacterial growth and increase the shelf life may be included along with reagents that stabilize the preparation, e.g., low concentrations of glycerol. It is specifically warned that freezing and thawing cycles could cause loss in efficiency of the formulation.

In yet another embodiment, the formulation of cationic amphiphiles and nucleic acid may be administered intravenously besides other routes such as intramuscular and intra peritonial. Further, the said formulation of amphiphiles may be administered to cells at a ratio of 0.1-0.5 microgram of DNA to 50,000 cells in an in vitro system. The amount of amphiphile could be varied from a lipid to DNA charge ratio of 0.5 to 8, considering one positive charge for one amphiphile molecule to one negative charge of a nucleotide base.

The plasmid used is a construct of an Cyto Megalo Virus promoter linked to a reporter gene β-galactosidase as supplied by Gibco BRL Life Technologies, USA (cat no. 10586-014). The plasmid could be of any construction and the example given is merely to demonstrate the efficiency of the amphiphilic formulation.

The invention further provides a process for the preparation of the said formulation comprising the steps of preparing a dispersion of a cationic amphiphile disclosed in the present invention; contacting said dispersion with a biologically active molecule to form a complex between said amphiphiles and said molecules and contacting cells with said complex thereby facilitating transfer of said biologically active molecules into the cells. The present invention also provides with various formulations that facilitate intracellular delivery of biologically active molecules.

Cellular Cytotoxicities of the Amphiphiles Disclosed in the Invention

The percent viabilities of cells in presence of various cationic amphiphiles disclosed herein were checked according to the standard protocol described in "Animal Cell Culture, 2nd Edition. Ed. I. R. L. Press, Oxford University Press (1977)". The transfection efficiencies of the cationic lipids were studied in the range of 0.45-7.2 nmole and within this limit, the cell cytotoxicities were observed to be minimal and the cell viabilities were determined to be more than 70%. The cationic amphiphiles were used with varying mole ratios of lipid to DNA using cholesterol as the neutral co-lipid.

Applications

The process of the present invention can be exploited for preparing cationic transfection lipids with polar shikimic acid head groups. The invention lipids are useful for delivering polyanions, polypeptides or nucleopolymers into cells. The cationic lipids disclosed herein can be used to deliver an expression vector into a cell for manufacturing or therapeutic use. The expression vectors can be used in gene therapy protocols to deliver a therapeutically useful protein to a cell or for delivering nucleic acids encoding therapeutically useful protein molecules that can generate an immune response in a host for vaccine or other immunomodulatory purposes according to the known methods. The vector-transformed cell can be used to produce commercially useful cell lines, such as a cell line for producing therapeutic proteins or enzymes (e.g. erythropoietin), growth factors (e.g. human growth hormone, G-CSF or interleukins) or other proteins.

The invention lipid-nucleic acid complexes can be used to construct cell lines for gene therapy applications in subjects such as humans or other species including murine, feline, bovine, equine, ovine or non-human primate species. The invention lipids can be used in presence of serum and will thus deliver polyanions into cells in tissue culture medium containing serum in vitro or in animal in vivo.

The invention lipids complexed with nucleopolymers can be used in antisense inhibition of gene expression in a cell by delivering an antisense oligonucleotide into the cell. A cell that is blocked for expression of a specific gene(s) is useful for manufacturing and therapeutic applications. Exemplary manufacturing uses include inhibiting protease synthesis in a cell to increase production (i.e., reduce target protein degradation caused by the protease) of a protein for a therapeutic or diagnostic application. Exemplary therapeutic applications include inhibiting synthesis of cell surface antigens (histocompatibility antigens, such as MHC class II genes, and the like) to reduce rejection and/or to induce immunologic tolerance of the cell after it is implanted into a subject or when the cell is transfected in vivo.

The invention lipids can be formulated with anionic, zwitterionic and lipophilic therapeutic agents including anticancer agents such as doxorubicin, a lipophilic compound, to obtain complexes comprising the invention lipids and a therapeutic agent(s). The invention lipids can be formulated with known antiviral agents such as HPMPC (9-(3-hydroxy-2-phosphonylmethoxy)propyl)cytosine), PMEA (9-(2-phosphonylmethoxy)ethyl)adenine), PMEG PMEA (9-(2-phosphonylmethoxy)ethyl)guanine), PMPA (9-(2-phosphonylmethoxy)propyl)adenine), AZT, 3TC, and their derivatives to obtain lipid complexes with antiviral agents. The invention lipids can be formulated with polyene antibiotics such as amphotericin B. Such formulations are useful for delivering the therapeutic agents into the cytoplasm of cells in vitro or in vivo. Complexes consisting of an invention cationic lipid and an anti-influenza agent can be used to deliver the antiviral agent to the lung, the primary site of infection. These complexes can be prepared by any of the techniques now known or subsequently developed for preparing lipid complexes containing therapeutic agents.

Table 1 summarizes the sizes and surface potentials of the present lipoplexes (lipid:DNA complexes) across varying lipid:DNA charge ratios in the presence of DMEM.

EXAMPLES

The following examples are given by way of illustration of the present invention and therefore should not be construed to limit the scope of the present invention. Synthetic procedures for representative cationic amphiphiles 1 and 2 disclosed in the present invention are described below in the examples 1 and 2. The structures of cationic lipids 1 and 2 are shown below.

1

2

Example 1

Synthesis of Lipid 1 (Scheme 1)

Step a (Scheme 1). HOBt and EDCI were added sequentially to an ice-cold and stirred solution of Shikimic acid (I, 0.2 g, 1.15 mmol) and N-2-aminoethyl-N,N-di-n-tetradecylamine (II, 0.46 g, 1.03 mmol, prepared as described by Valluripalli, V. et al. in *Gene. Ther,* 2003, 10, 1206-1215) in a mixture of dry DCM/DMF (5:1 v/v). The reaction mixture was stirred at 0° C. for 1 h, the temperature gradually raised to room temp and the reaction mixture was kept stirred at room temperature for 12 h. The reaction mixture was concentrated and the residue was taken in chloroform (100 mL) and washed sequentially with water (3×100 mL) followed by saturated sodium bicarbonate (2×100 mL) and finally washed with brine solution (2×100 mL). The organic layer was separated, dried over anhydrous $Na_2SO_4$, filtered, and concentrated. The residue upon column chromatographic purification (using 60-120 mesh size silica gel and 6-7 MeOH:$CHCl_3$ as eluent) afforded pure compound as a solid (0.23 g, 33% yield, $R_f$=0.5, 15:85, v/v, MeOH:$CHCl_3$).

$^1H$ NMR (300 MHz, $CDCl_3$): δ/ppm=0.9 [t, 6H, $CH_3$—$(CH_2)^{11}$]; 1.17-1.40 [m, 44H, —$(CH_2)_{11}$]; 1.40-1.70

[m, 4H, N(—CH$_2$—CH$_2$—)$_2$]; 2.0-2.20 [m, 2H, H-6 and H-6$^1$]; 2.60-2.90 [m, 4$\overline{\text{H}}$, N(CH$_2$—CH$_2$—)$_2$]; 2.90-3.00 [2H, N(CH$_2$—CH$_2$—NH—CO); 3.40-3.65 [m, 3H, N(CH$_2$—CH$_2$—NH—CO and H-3]; 3.85-4.40 [2 brs, 2H, H-4 and H-5]; 5.00-5.40 [brs, 3 OH]; 6.40-6.50 [brs, 1H, H-2]; 7.80-7.95- [brs, 1H, CONH].

FABMS (LSIMS): m/z: 610 [M]$^+$+1 for C$_{37}$H$_{72}$O$_4$N$_2$Cl

Step b (Scheme 1). The pure intermediate tertiary amine obtained above in step a (0.11 g, 0.18 mmol) was dissolved in excess of methyl iodide (6 mL) and the reaction mixture was stirred at room temp for overnight. The reaction mixture was concentrated and the residue upon column chromatography purification (using 60-120 mesh size silica gel and 10:90 methanol-chloroform, v/v, as eluent) followed by chloride ion exchange (over Amberlyst A-26 using methanol as the eluent) afforded the pure title lipid 1 as a solid (0.048 g, 43% yield, R$_f$=0.5, 15:85, v/v, methanol/chloroform).

$^1$H NMR (300 MHz, CDCl$_3$): δ/ppm=0.9 [t, 6H, CH$_3$—(CH$_2$)$_{11}$—]; 1.15-1.80 [m, 48H, —(CH$_2$)$_{12}$]; 2.10-2.80 [2 brs, 2H, H-6 and H-6$^{\cdot 1}$]; 3.00-3.40 [m, 6H, N(CH$_2$—CH$_2$—)$_2$ and N(CH2—CH$_2$—NH—CO]; 3.60-4.60 [m, 8H, CH$_3$N$^+$, N$^+$(CH$_2$—CH$_2$—NH—CO), H-3, H-4 & H-5); 5.60-6.40 [3 brs, 3OH]; 6.40-6.60 [brs, 1H, H-2]; 8.00-8.20 [brs, 1H, CONH].

FABMS (LSIMS): m/z: 623 [M]$^+$ for C$_{38}$H$_{75}$O$_4$N$_2$Cl.

Example 2

Synthesis of Lipid 2 (Scheme 1): The lipid 2 (solid) was synthesized following the same synthetic procedure as described above for preparing the lipid 1 using N-2-aminoethyl-N,N-di-n-hexadecylamine (II, with an overall yield of 43%). All the isolated intermediates gave spectroscopic data in agreement with their assigned structures shown in Scheme I.

$^1$H NMR (300 MHz, CDCl$_3$) of intermediate III (Scheme I where R=n-C$_{16}$H$_{33}$): =0.9 [t, 6H, CH$_3$—(CH$_2$)$_{11}$—]; 1.00-1.40 [m, 52H, —(CH$_2$)$_{13}$]; 1.50-1.80 [m, 4H, N(—CH$_2$—CH$_2$—)$_2$]; 2.0-2.3 [m, 2H, H-6 and H-6$^{\cdot 1}$]; 2.80-2.95 [m, 4H, N(CH$_2$—CH$_2$—)$_2$]; 3.00-3.10 [2H, N(CH$_2$—CH$_2$—NH—CO]; 3.40-3.70 [m, 3H, N(CH$_2$—CH$_2$—NH—CO and H-3]; 3.85-4.40 [2 brs H-4 and H-5]; 4.50-5.20 [brs, 3 OH]; 6.40-6.60 [brs, 1H, H-2]; 7.75-8.00 [brs, 1H, CONH].

FABMS (LSIMS): m/z: 666 [M]$^+$+1 for C$_{41}$H$_{80}$O$_4$N$_2$Cl.

$^1$H NMR (300 MHz, CDCl$_3$): (lipid 2) Δ/ppm=0.9 [t, 6H, CH$_3$—(CH$_2$)$_{11}$]; 1; 1.10-1.80 [m, 56H, —(CH$_2$)$_{14}$]; 2.10-2.90 [2 brs, 2H, H-6 and H-6$^{\cdot 1}$]; 3.00-3.40 [m, 6H, N(CH$_2$—CH$_2$—)$_2$ and N(CH$_2$—CH$_2$—NH—CO]; 3.60-4.60 [m, 8H, CH$_3$N$^+$, N$^+$(CH$_2$—CH$_2$—NH—CO), H-3 & H-4 & H-5); 5.00-5.90 [2 brs, 3 OH]; 6.50-6.60 [brs, 1H, H-2]; 8.00-8.30 [brs, 1H, CONH].

FABMS (LSIMS): m/z: 680 [M]$^+$+1 for C$_{42}$H$_{83}$O$_4$N$_2$Cl.

Example 3

Figure 1A:
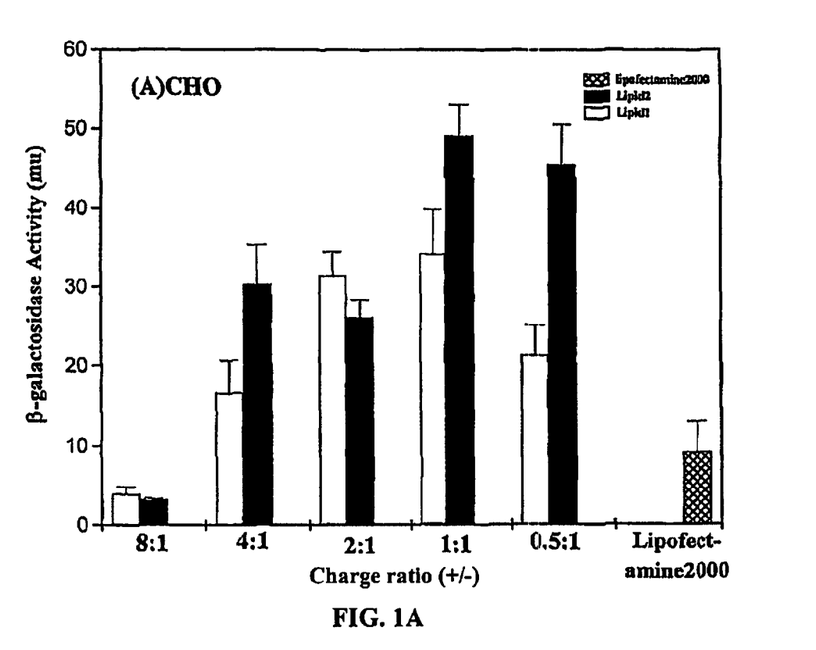
FIGS. 1A-C summarize the in vitro gene delivery efficiencies for the cationic amphiphiles 1 and 2 disclosed in the present invention and that of Lipofectamine 2000, one of the most widely used commercially available transfection lipids.

Preparation of lipid:DNA complexes and CHO cell transfection. Cells were seeded at a density of 20000 cells (for CHO, MCF-7) and 15000 cells (for COS-1) per well in a 96-well plate 18-24 hours before the transfection. 0.3 µg of plasmid DNA was complexed with varying amounts of lipids (0.45-7.2 mmol) in plain DMEM medium (total volume made upto 100 µl) for 30 minutes. The charge ratios were varied from 0.5:1 to 8:1, (+/−) over these ranges of the lipids. The complexes were then added to the cells. After 4 h of incubation, 100 µl of DMEM with 20% FBS was added to the cells. The medium was changed to 10% complete medium after 24 h and the reporter gene activity was estimated after 48 h. The cells were washed twice with PBS (100 µl each) and lysed in 50 µl lysis buffer [0.25 M Tris-HCl pH 8.0, 0.5% NP40]. Care was taken to ensure complete lysis. The β-galactosidase activity per well was estimated by adding 50 µl of 2×-substrate solution [1.33 mg/ml of ONPG, 0.2 M sodium phosphate (pH 7.3) and 2 mM magnesium chloride] to the lysate in a 96-well plate. Adsoption at 405 nm was converted to β-galactosidase units using a calibration curve constructed with pure commercial β-galacttosidase enzyme. The values of β-galactosidase units in triplicate experiments assayed on the same day varied by less than 20%. The transfection experiment was carried in triplicate and the transfection efficiency values shown in FIG. 1A are the average of triplicate experiments performed on the same day. Each transfection experiment was repeated two times and the day to day variation in average transfection efficiency was found to be within 2-fold. The transfection profiles obtained on different days were identical FIG. 1A shows representative transfection results obtained with cationic lipids 1 and 2. As shown in FIG. 1A, the in vitro transfection efficiency of cationic lipids 1 and 2 are better than that of Lipofectamine2000, one of the most extensively used commercially available liposomal transfection kits.

Example 4

Figure 1B:
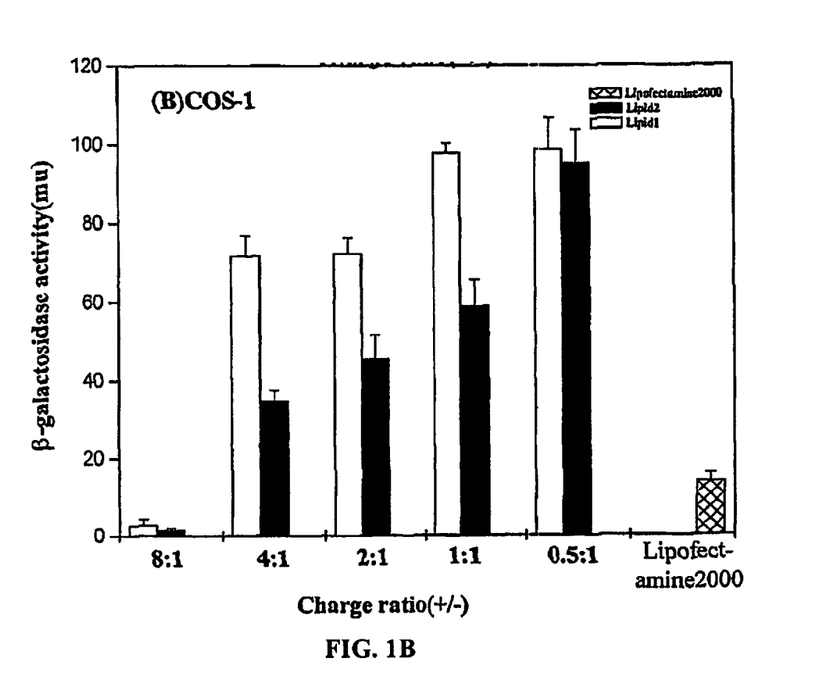

Preparation of lipid:DNA complexes and COS—I cell transfection. Cells were seeded at a density of 15000 cells per well in a 96-well plate 18-24 hours before the transfection. 0.3 µg of plasmid DNA was complexed with varying amounts of lipids (0.45-7.2 mmol) in plain DMEM medium (total volume made upto 100 µl) for 30 minutes. The charge ratios were varied from 0.5:1 to 8:1 (+/−) over these ranges of the lipids. The complexes were then added to the cells. After 4 h of incubation, 100 µl of DMEM with 20% FBS was added to the cells. The medium was changed to 10% complete medium after 24 h and the reporter gene activity was estimated after 48 h. The cells were washed twice with PBS (100 µl each) and lysed in 50 µl lysis buffer [0.25 M Tris-HCl pH 8.0, 0.5% NP40]. Care was taken to ensure complete lysis. The β-galactosidase activity per well was estimated by adding 50 µl of 2×-substrate solution [1.33 mg/ml of ONPG, 0.2 M sodium phosphate (pH 7.3) and 2 mM magnesium chloride] to the lysate in a 96-well plate. Adsoption at 405 m was converted to β-galactosidase units using a calibration curve constructed with pure commercial β-galacttosidase enzyme. The values of β-galactosidase units in triplicate experiments assayed on the same day varied by less than 20%. The transfection experiment was carried in triplicate and the transfection efficiency values shown in FIG. 1B are the average of triplicate experiments performed on the same day. Each transfection experiment was repeated two times and the day to day variation in average transfection efficiency was found to be within 2-fold. The transfection profiles obtained on different days were identical FIG. 1B shows representative transfection results obtained with cationic lipids 1 and 2. As shown in FIG. 1B, the in vitro transfection efficiency of cationic lipids 1 and 2 are better than that of Lipofectamine2000, one of the most extensively used commercially available liposomal transfection kits.

Example 5

Figure 1C:
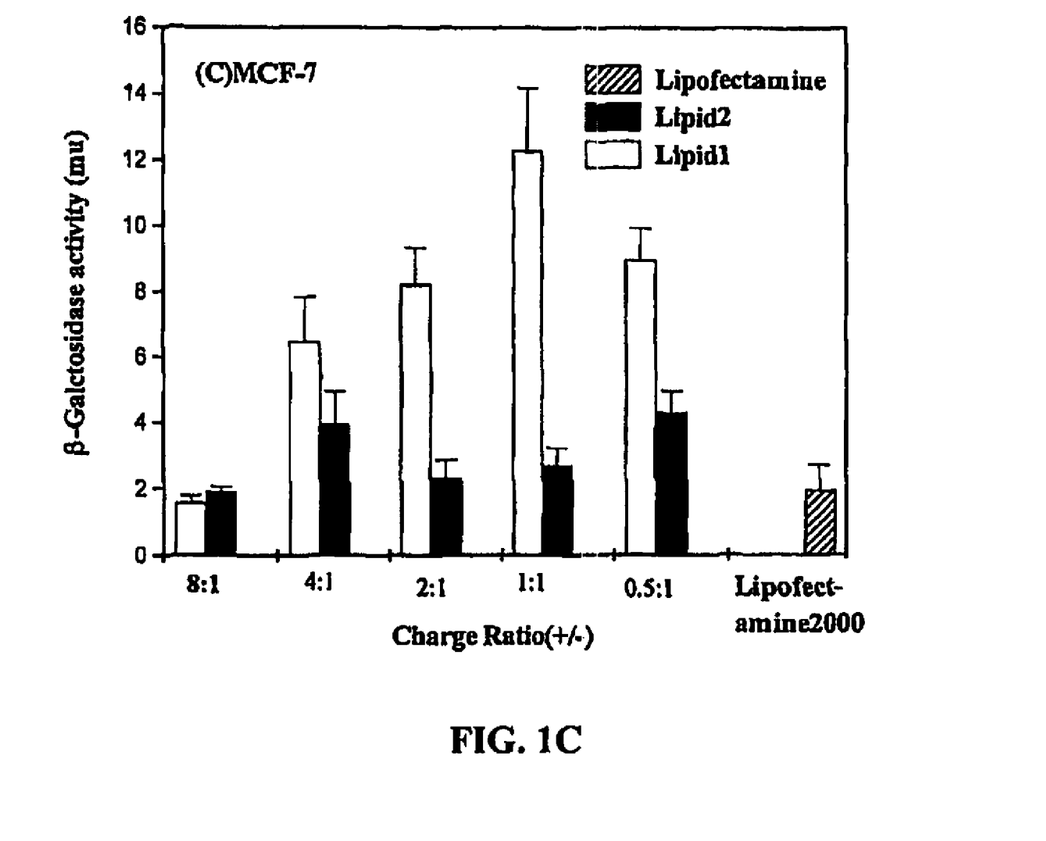

Preparation of lipid:DNA complexes and MCF-7 cell transfection. Cells were seeded at a density of 20000 cells per well in a 96-well plate 18-24 hours before the transfection. 0.3

µg of plasmid DNA was complexed with varying amounts of lipids (0.45-7.2 mmol) in plain DMEM medium (total volume made upto 100 µl) for 30 minutes. The charge ratios were varied from 0.5:1 to 8:1 (+/−) over these ranges of the lipids. The complexes were then added to the cells. After 4 h of incubation, 100 µl of DMEM with 20% FBS was added to the cells. The medium was changed to 10% complete medium after 24 h and the reporter gene activity was estimated after 48 h. The cells were washed twice with PBS (100 µl each) and lysed in 50 µl lysis buffer [0.25 M Tris-HCl pH 8.0, 0.5% NP40]. Care was taken to ensure complete lysis. The β-galactosidase activity per well was estimated by adding 50 µl of 2×-substrate solution [1.33 mg/ml of ONPG, 0.2 M sodium phosphate (pH 7.3) and 2 mM magnesium chloride] to the lysate in a 96-well plate. Adsoption at 405 m was converted to β-galactosidase units using a calibration curve constructed with pure commercial β-galacttosidase enzyme. The values of β-galactosidase units in triplicate experiments assayed on the same day varied by less than 20%. The transfection experiment was carried in triplicate and the transfection efficiency values shown in FIG. 1B are the average of triplicate experiments performed on the same day. Each transfection experiment was repeated two times and the day to day variation in average transfection efficiency was found to be within 2-fold. The transfection profiles obtained on different days were identical FIG. 1C shows representative transfection results obtained with cationic lipids 1 and 2. As shown in FIG. 1C, the in vitro transfection efficiency of cationic lipids 1 and 2 are better than that of Lipofectamine2000, one of the most extensively used commercially available liposomal transfection kits.

Example 6

Transfection assay by Whole Cell Histochemical X-gal Staining of CHO Cells: CHO Cells expressing β-galactosidase were histochemically stained with the substrate 5-bromo-4-chloro-3-indolyl-β-D-galactopyranoside (X-gal, as described in Schoen, P et al *Gene Ther.* 1999, 6, 823-832). Briefly, 48 hrs after transfection with lipoplexes in 96 well plates, the cells were washed two times (2×100 µL) with phosphate-buffered saline (PBS, 137 mM NaCl, 2.7 mM KCl, 10 mM $Na_2HPO_4$, 2 mM $KH_2PO_4$, pH 7.4) and fixed with 0.5% glutaraldehyde in PBS (225 µL). After 15 minutes incubation at room temperature, the cells were washed again with PBS three times (3×250 µL) and subsequently, were stained with 1.0 mg/mL X-gal in PBS containing 5.0 mM $K_3[Fe(CN)_6]$, and 5.0 mM $K_4[Fe(CN)_6]$ and 1 mM $MgSO_4$ for 2-4 hours at 37° C. Blue colored cells were identified by light microscope (Leica, Germany).

Figure 2:
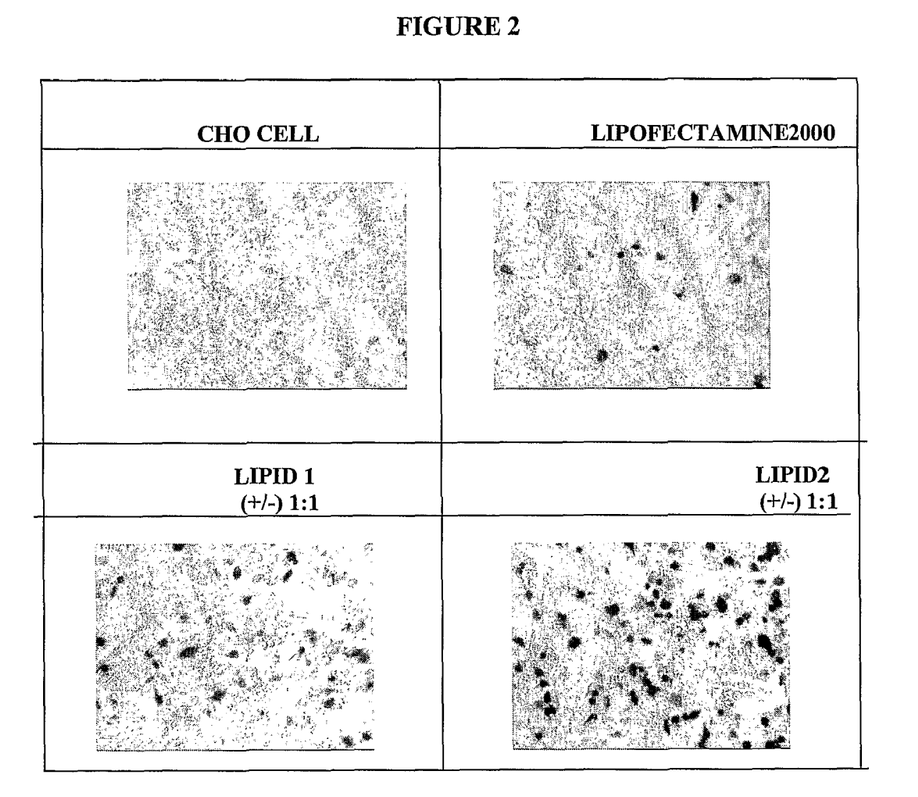
FIG. 2 shows the histochemical whole cell staining of transfected CHO cells with lipids 1 and 2 at lipid:DNA charge ratios at 1:1.

FIG. 2 shows the histochemical whole cell X-gal staining of the transfected CHO cells with lipids 1 and 2 at lipid:DNA charge ratios at 1:1. As shown in FIG. 2, the number of X-gal stained CHO cells transfected with cationic lipids 1 & 2 are significantly higher than those transfected with commercially available Lipofectamine2000.

Example 7

Per Cent Cell Viabilities. Cytotoxicities of the lipids 1-2 were evaluated by the 3-(4,5-dimethylthiazol-2-yl)-2,5-diphenyltetrazolium bromide (MTT) reduction assay. The assay was performed in 96-well plates by maintaining the same ratio of number of cells to amount of cationic lipid, as used in the transfection experiments. MTT was added 3 h after addition of cationic lipid to the cells. Results were expressed as percent viability [$A_{540}$ (treated cells)-background/$A_{540}$ (untreated cells)-background]×100.

Figure 3:
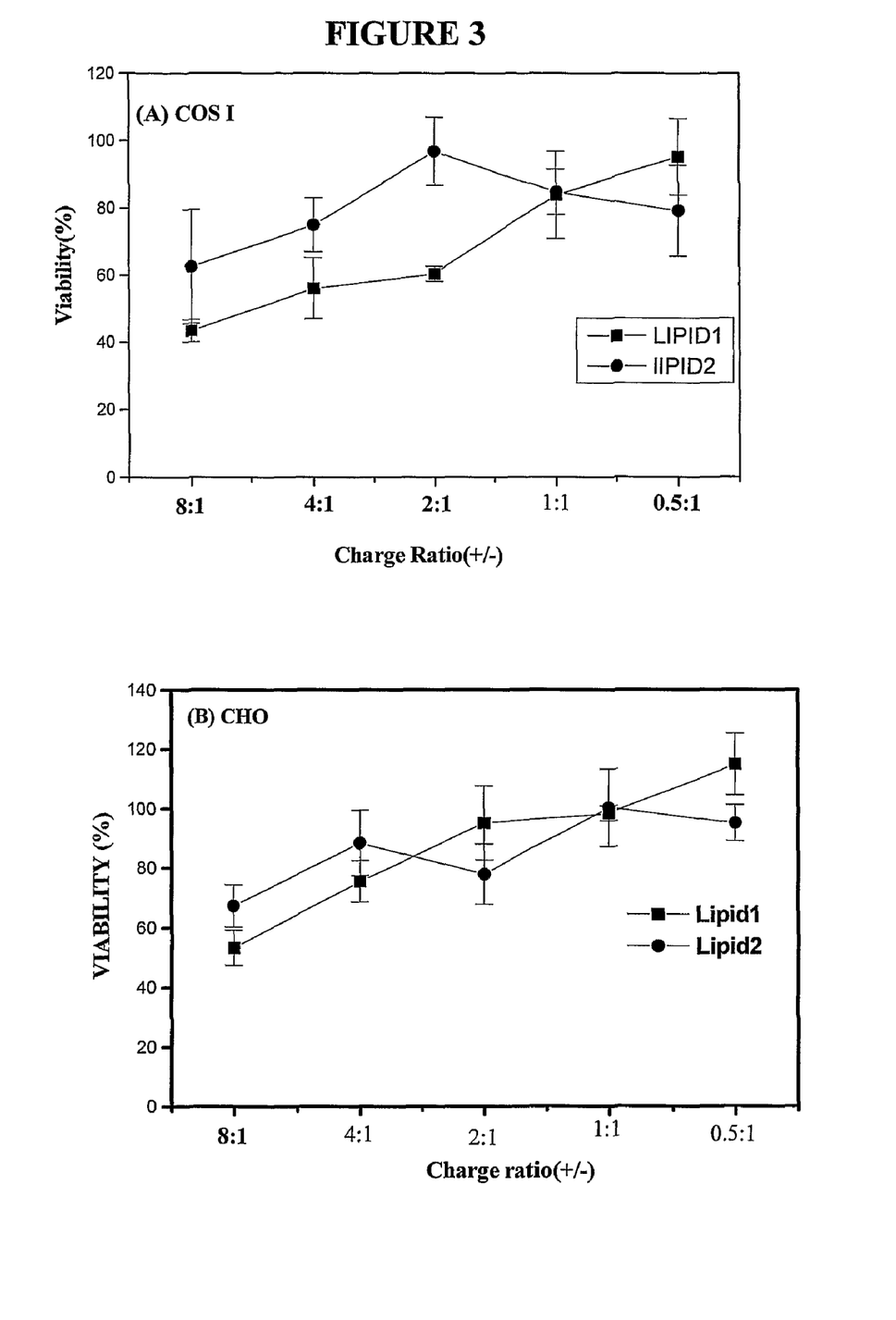
FIG. 3 provides the in vitro cellular toxicity data of the cationic amphiphiles 1 and 2 disclosed in the present invention.

FIG. 3 summarizes the results of the MTT based COS-1 & CHO cell viability assays for lipids 1 and 2 across the varying lipid:DNA charge ratios. Lipids 1 and 2 showed least cytotoxicity even at a 8:1 lipid:DNA charge ratio.

Example 8

Preparation of lipid:DNA complexes and CHO cell transfection in the presence of serum. CHO Cells were seeded at a density of 20000 cells in a 96-well plate 18-24 hours before the transfection. 0.3 µg of plasmid DNA was complexed with varying amounts of lipids (0.9-0.45 nmol) in plain DMEM medium (total volume made upto 100 µl) for 30 minutes. The charge ratios were varied from 0.5:1 to 1:1 (+/−) over these ranges of the lipids. The complexes were then added to the cells, followed by addition of 100 µl of DMEM with 60% FBS for 30% serum experiment and addition of 100 µl FBS for 50% serum experiment. After 4 h of incubation medium was changed to 200 µl of DMEM containing 10% serum. After 24 h the medium was changed and the reporter gene activity was estimated after 48 h as mentioned above (Example 1).

Figure 4:
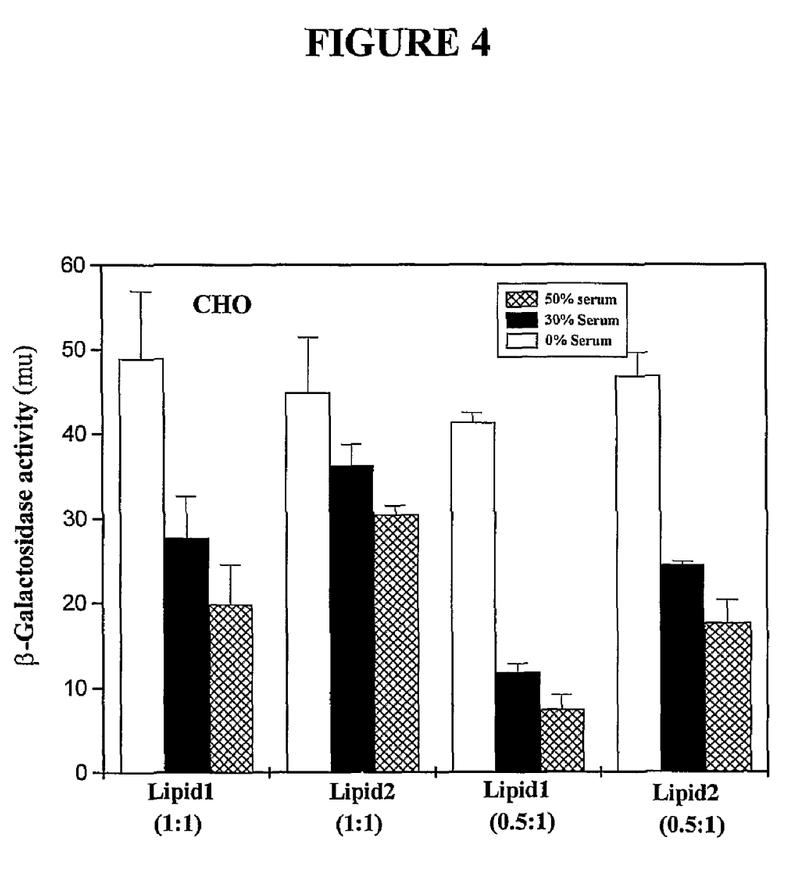
FIG. 4 summarizes the in vitro gene delivery efficiencies for the cationic amphiphiles 1 and 2 in the presence of serum.

The representative efficacies of lipids 1 & 2 in transfecting CHO cells in presence of serum are depicted in FIG. 4. The results summarized in FIG. 4 demonstrated that the presently described cationic lipids are capable of transfecting cells in presence of serum too.

Example 9

Preparation of lipid:DNA complexes and CHO cell transfection in the absence of co-lipid. CHO cells were seeded at a density of 20000 cells in a 96-well plate 18-24 hours before the transfection. 0.3 µg of plasmid DNA was complexed with varying amounts of lipids (0.9-0.45 nmol) in plain DMEM medium (total volume made upto 100 µl) for 30 minutes. The charge ratios were varied from 0.5:1 to 1:1 (+/−) over these ranges of the lipids. After 4 h of incubation, 100 µl of DMEM with 20% FBS was added to the cells. The medium was changed to 10% complete medium after 24 h and the reporter gene activity was estimated after 48 h as mentioned above (Example 1)

Figure 5:
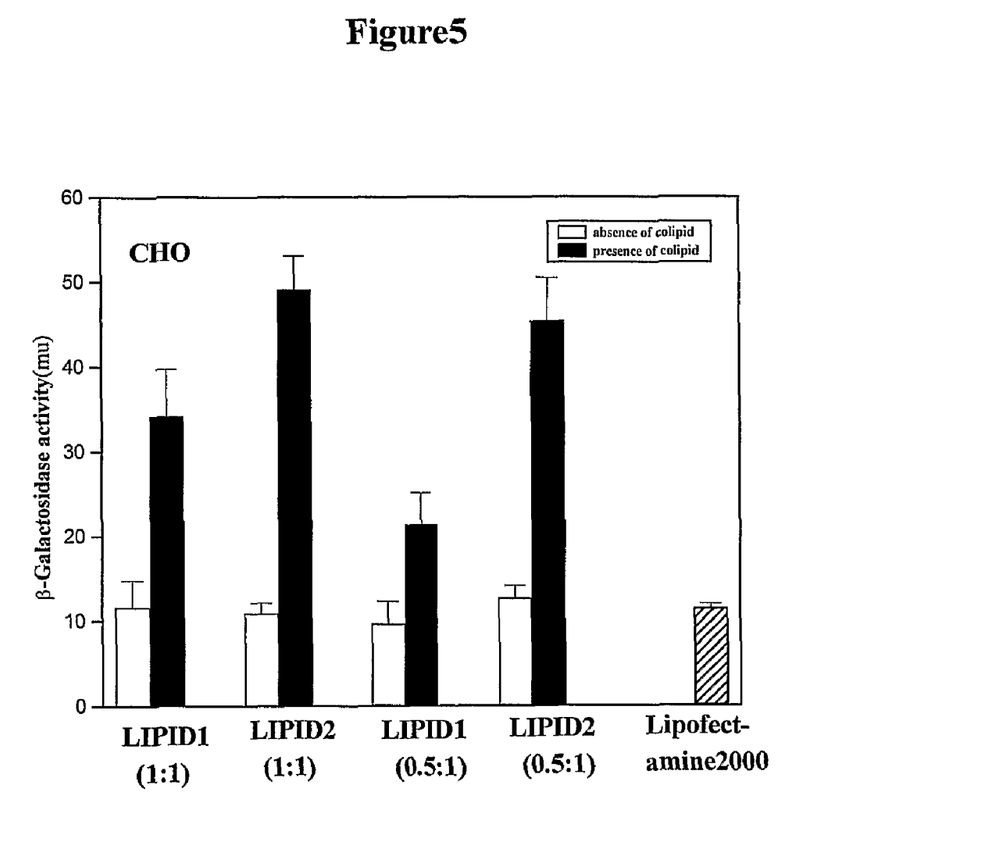
FIG. 5 summarizes the in vitro gene delivery efficiencies for the cationic amphiphiles 1 and 2 in the presence and absence of co-lipid.
Figure 6A:
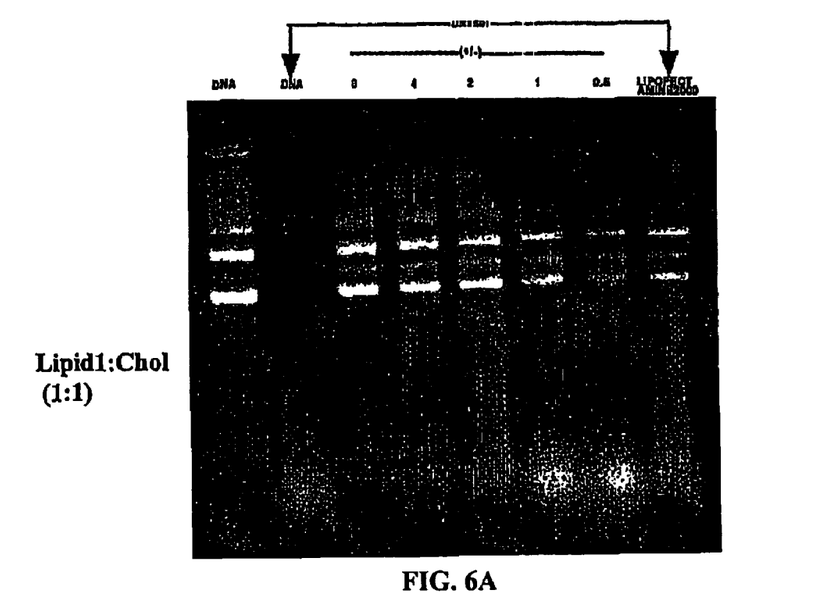
FIGS. 6A-D are a depiction of the Electrophoretic Gel patterns for lipoplex-associated DNA in DNase 1 sensitivity assay. The lipid:DNA charge ratios are indicated at the top of each lane. The details of treatment are as described in the example section.
Figure 6B:
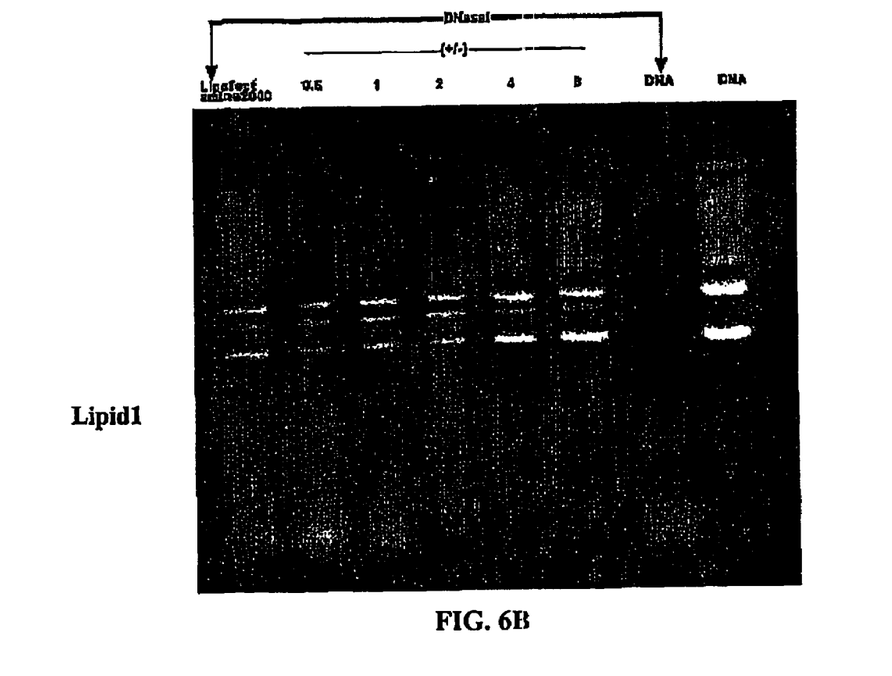
Figure 6C:
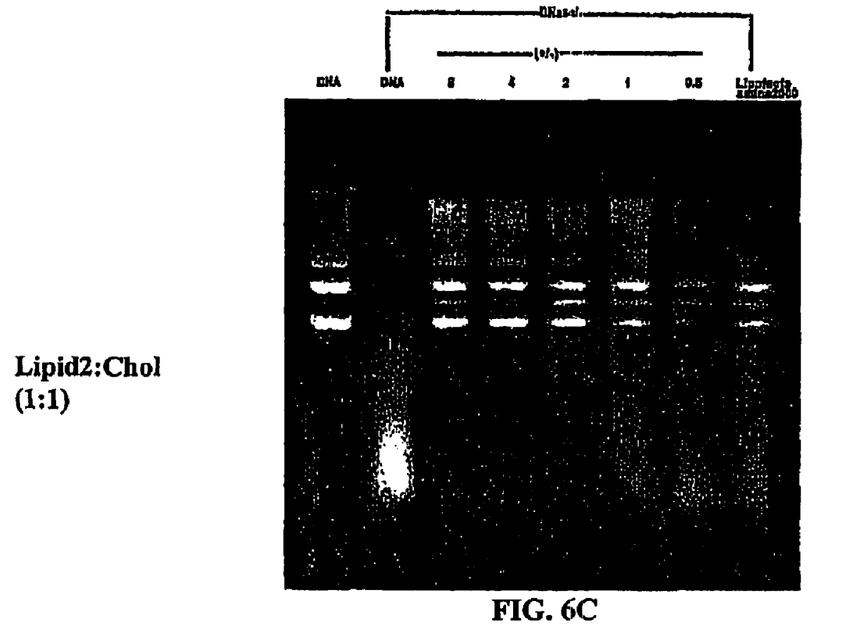
Figure 6D:
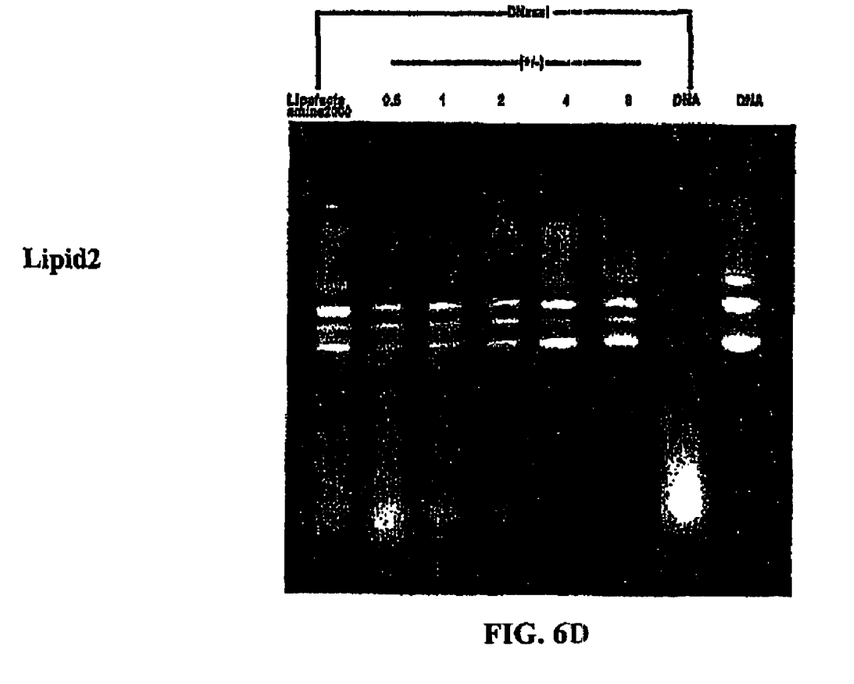

FIG. 5 shows representative transfection results obtained with cationic lipids 1 and 2 in the presence and absence of co-lipid at 1:1 and 0.5:1 charge ratios. Interestingly, while most of the cationic lipids used for transfecting cells work only when used in combination with co-lipids, both lipids 1 and 2 showed the same activity as that of commercially available Lipofectamine even in absence of any co-lipids (FIG. 5).

Example 10

Evaluation of Lipid:DNA interactions by the DNase 1 sensitivity assay. Briefly, in a typical assay, pCMV-β-gal (1000 ng) was complexed with the varying amount of cationic lipids (using indicated lipid:DNA charge ratios in FIGS. 6A-D) in a total volume of 30 µL in Hepes buffer, pH 7.40 and incubated at room temperature for 30 min on a rotary shaker. Subsequently, the complexes were treated with 10 µL DNase I (at a final concentration of 1 µg/mL) in presence of 20 niM MgC12 and incubated for 20 min at 37° C. Thi reactions were then halted by adding EDTA (to a final concentration of 50 mM) and incubated at 60° C. for 10 min in a water bath. The aqueous layer was washed with 50 µL of phenol: chloroform (1:1, v/v) and centrifuged at 10,000 g for 5 min. The aqueous supernatants were seperated, loaded (20 µL for lipids 1 and 2)

on a 0.8% agarose gel and electrophoresed at 80V for 2 h. The electrophoretic gel patterns summarized in FIGS. 6A-D demonstrated that the accessibility of lipid associated DNA to DNase I depends on lipid:DNA charge ratios. The results summarized in FIGS. 6A-D demonstrated that for the presently described lipids 1 & 2, the DNA becomes strongly associated with lipoplexes and thereby inaccessible to DNase I beyond lipid:DNA charge ratio 2.0:1. However, significant DNA dissociation occurs at 1:1 or lower lipid:DNA charge ratios (FIGS. 6A-D).

Example 11

Surface charge ($\xi$) and sizes of Lipid:DNA complexes. The sizes and the surface charges (zeta potentials) and lipoplexes were measured by photon correlation spectroscopy and electrophoretic mobility on a Zeta sizer $3000HS_A$ (Malvern UK). The sizes were measured in DMEM with a sample refractive index of 1.59 and a viscosity of 0.89. The system was calibrated by using the 200 nm ±5 nm polystyrene polymer (Duke Scientific Corps. Palo Alto, Calif.). The diameters of lipoplexes were calculated by using the automatic mode. The zeta potential was measured using the following parameters: viscosity, 0.89 cP; dielectric constant, 79; temperature, 25° C.; F(Ka), 1.50 (Smoluchowski); maximum voltage of the current, V. The system was calibrated by using DTS0050 standard from Malvern, UK. Measurements were done 10 times with the zero field correction. The potentials were calculated by using the Smoluchowski approximation. The results summarized in Table 1 show that the transaction competent lipoplexes were of sizes in the range 200-500 nm and were negatively charged in presence of DMEM.

Figure Legends

FIGS. 1A-C. In Vitro Transfection efficiencies of lipids 1 and 2 in CHO (A), COS-I (B) and MCF-7 (C) cells using cholesterol as colipid (at lipid:cholesterol mole ratio of 1:1). Units of μ-galactosidase activity were plotted against the varying Lipid to DNA (+/−) charge ratios. The o-nitrophenol formation (micromoles of o-nitrophenol produced per 5 min) was converted to (μ-galactosidase activity units using standard curve obtained with pure (commercial) μ-galactosidase. The transfection efficiencies of commercially available Lipofectamine2000 are shown for comparison sake. The transfection values shown are average of triplicate experiments performed on the same day.

FIG. 2. Histochemical whole cell staining of transfected CHO cells with X-gal with lipids 1 and 2 at lipid:DNA charge ratios at 1:1. Cells expressing β-galactosidase were stained with X-gal as described in the text.

FIG. 3. MTT-assay based percent cell viabilities of lipid 1 and 2 in representative COS-1 (A), CHO (B) cells. The percent cell viability values shown are average of triplicate experiments performed on the same day.

FIG. 4. In Vitro Transfection efficiencies of lipids 1 and 2 in CHO Cells in presence of serum. Units of β-galactosidase activity were plotted against the varying Lipid to DNA (+/−) charge ratios. The o-nitrophenol formation (micromoles of o-nitrophenol produced per 5 min) was converted to β-galactosidase activity units using standard curve obtained with pure (commercial) β-galactosidase. The transfection values shown are average of triplicate experiments performed on the same day FIG. 5. Transfection efficiencies of lipids 1 and 2 in the absence of co-lipid in CHO cells. Units of β-galactosidase activity were plotted against the varying Lipid to DNA (+/−) charge ratios. The o-nitrophenol formation (micromoles of o-nitrophenol produced per 5 min) was converted to β-galactosidase activity units using standard curve obtained with pure (commercial) β-galactosidase. The transfection values shown are average of triplicate experiments performed on the same day

FIGS. 6A-D. Electrophoretic Gel patterns for lipoplex-associated DNA in DNase I sensitivity assay. The lipid:DNA charge ratios are indicated at the top of each lane.

TABLE 1

| Lipids | Lipid:DNA (+/−) 0.5:1 | Lipid:DNA (+/−) 1:1 | Lipid:DNA (+/−) 2:1 | Lipid:DNA (+/−) 4:1 | Lipid:DNA (+/−) 8:1 |
|---|---|---|---|---|---|
| A. sizes of Lipoplexe(presence of DMEM)* | | | | | |
| 1 | 246.5 ± 3.1 | 265.1 ± 2.2 | 405.5 ± 14.1 | 901.7 ± 51.2 | 993.5 ± 62.3 |
| 2 | 485.7 ± 6.2 | 466.8 ± 13.9 | 569.9 ± 30 | 880 ± 88 | 908.7 ± 89 |
| B. Zeta Potentials ($\xi$) of lipioplexes *(presence of DMEM) | | | | | |
| 1 | −35.6 ± 1.3 | −38.0 ± 0.8 | −38.3 ± 0.8 | 12.6 ± 6.4 | 18.9 ± 5.1 |
| 2 | −37.9 ± 1.1 | −38.7 ± 0.7 | −3.4 ± 1.1 | 15.5 ± 6.6 | 16.4 ± 4.8 |

*Sizes and $\xi$ potentials were measured by laser light scattering technique using Zetasizer 3000 A (Malvern Instruments, UK). Values shown are the averages obtained from three (size) and ten (zeta potential) measurements.

We claim
1. A process for synthesis of a compound comprising a shikimic acid head group based cationic amphiphile of formula A:

wherein each of $R_1$ and $R_2$ is independently hydrogen or a lipophilic moiety containing at least eight carbon atoms, provided both $R_1$ and $R_2$ are not hydrogen; $R_3$ is an alkyl group ($C_1$-$C_5$, straight or branched); n is an integer between 7 and 21; and X is a chlorine or bromine atom comprising:
   (a) coupling a mixed primary-tertiary lipophilic aliphatic alkyl amine containing saturated or unsaturated aliphatic hydrocarbon chains with Shikimic acid in a polar aprotic solvent in presence of amide bond forming reagents to obtain the corresponding aliphatic hydrophobic amide intermediate;

(b) quaternizing the hydrophobic amide obtained in step (a) with excess of appropriate alkyl iodides to obtain the corresponding quaternized amphiphilic ammonium iodides intermediate; and (c) subjecting the quaternized amphi philic intermediate obtained above in step (b) to ion exchange chromatography halide ion exchange resin and mixed polar organic solvent as the eluent.

2. The process of claim 1, wherein in the compound of Formula A one or both of $R_1$ and $R_2$ are independently an 8-22 carbon containing alkyl, mono-, di- and/or tri-unsaturated alkenyl ($C_8$-$C_{22}$).

3. The process of claim 1, wherein in the compound of Formula A n=13 or 15, $R_3$ is independently a methyl, ethyl, or n-propyl group, and $X^-$ is a chloride or bromide ion.

4. The process of claim 1, wherein the compound of Formula A is further defined as being of formula 1 or 2:

1

2

5. The process of claim 1, wherein in the compound of Formula A the lipophilic $R_1$ and $R_2$ groups are independently saturated $C_8$-$C_{22}$ alkyl groups and/or unsaturated $C_8$-$C_{22}$ alkenyl groups containing 1, 2, or 3 double bonds.

6. The process of claim 1, wherein one or both of $R_1$ and $R_2$ are independently an 8-22 carbon containing alkyl, mono-, di- and/or tri-unsaturated alkenyl ($C_8$-$C_{22}$)

7. The process of claim 1, wherein saturated or unsaturated aliphatic hydrocarbon chains of the mixed primary-tertiary amine comprise between 8 and 22 carbon atoms.

8. The process of claim 1, wherein the polar aprotic solvent in which the reaction is carried out in step (a) comprise dimethyl formamide, dimethylsulphoxide, pyridine, and/or triethyl amine.

9. The process of claim 1, wherein the reaction of step (a) is carried out at a temperature between 0° C. to 80° C.

10. The process of claim 1, wherein the quaternization of the intermediate hydrophobic amide is carried out at a temperature between −10° C. to 50° C.

11. The process of claim 1, wherein the halide ion exchange resin used in step (c) comprises chloride and/or bromide ion exchange resins.

12. The process of claim 1, wherein the organic solvents used as ingredients of the polar eluent comprise methanol, ethanol, chloroform, dichloro methane, and/or ethyl acetate.

* * * * *